United States Patent [19]
Jackson

[11] Patent Number: 5,316,638
[45] Date of Patent: May 31, 1994

[54] TREATMENT OF CARBOHYDRATES

[76] Inventor: Peter Jackson, 8 Oslars Way, Fulbourn Cambridge, Great Britain, CB1 5DS

[21] Appl. No.: 844,571
[22] PCT Filed: Sep. 20, 1990
[86] PCT No.: PCT/GB90/01449
  § 371 Date: Mar. 27, 1992
  § 102(e) Date: Mar. 27, 1992
[87] PCT Pub. No.: WO91/05265
  PCT Pub. Date: Apr. 18, 1991

[30] Foreign Application Priority Data

Sep. 27, 1989 [GB] United Kingdom ............... 8921818

[51] Int. Cl.$^5$ .............................................. C25B 7/00
[52] U.S. Cl. ................................................ 204/182.8
[58] Field of Search ..................................... 204/182.8

[56] References Cited

U.S. PATENT DOCUMENTS 4,589,965 5/1986 Kreisher ........................... 204/182.8
5,019,231 5/1991 Brandley et al. ............... 204/299 R

FOREIGN PATENT DOCUMENTS

A20136153 9/1984 European Pat. Off. .
WO88/10422 12/1988 World Int. Prop. O. .
8403055 12/1988 World Int. Prop. O. .
WO91/05256 4/1991 World Int. Prop. O. .

OTHER PUBLICATIONS

Turnbull and Gallagher, "Oligosaccharide mapping of heparin sulphate by polyacrylamide-gradient-gel electrophoresis and electrotransfer to nylon membrane," *Biochem. J.* 251:597–608 (1988).
Lutsik et al., "The use of lectins in the study of human red blood cell membrane glycoproteins," CA 108(11):91259d.
Stocker, et al., "Characterization of Biotin–Labeled Proteoglycans by Electrophoretic Separation on Minigels and Blotting onto Nylon Membranes prior and after Enzymatic Digestion", *Analytical Biochemistry* 179:245–250 (1989).
Hakim & Lindhardt, "Isolation and recovery of acidic oligosaccharides from polyacrylamide gels by semi-dry electrotransfer", *Electrophoresis* 11:23–28 (1990).
Peter Jackson, "The use of polyacrylamide-gel electrophoresis for the high-resolution separation of reducing saccharides labelled with the fluorophore 8-aminonaphthalene-1,3,6-trisulphonic acid", *Biochem. J.* 270:705–713 (1990).
Jackson & Thompson, "The immunodetection of brain proteins blotted onto nitrocellulose from fixed and stained two-dimensional polacrylamide gels", *Electrophoresis* 5:35–42 (1984).
Neville, David M., "Molecular Weight Determination of Protein-dodecyl Sulfate Complexes by Gel Electrophoresis in a Discontinuous Buffer System", *Jour. of Biol. Chem.* 246:6328–6334 (1971).
Laemmli, U. K., "Clevage of structural Proteins during the Assembly of the Head of Bacteriophage T4", *Nature* 227:680–685 (1970).

*Primary Examiner*—John F. Niebling
*Assistant Examiner*—Cybille Delacroix-Muirheid
*Attorney, Agent, or Firm*—Limbach & Limbach

[57] ABSTRACT

Charged carbohydrate substances which have been run on an electrophoretic gel are transferred onto a porous membrane by a blotting technique such as an electrotransfer technique. This enables recovery of carbohydrate substances from a gel in a form that is well suited to storage or further treatment, for example analysis by probing with labelled protein probes.

15 Claims, 7 Drawing Sheets

Galβ1–4GlcNAcβ1–3Galβ1–4Glc
    3
    |
    1
Fuc α

TREATMENT OF CARBOHYDRATES

FIELD OF THE INVENTION

This invention concerns treatment of carbohydrates, for analytical and other purposes.

BACKGROUND TO THE INVENTION

International Publication No WO88/10422 discloses, inter alia, techniques for analysing carbohydrate structures or distinguishing or separating carbohydrate substances, involving applying carbohydrate substances to an electrophoretic gel and running the gel to cause differential migration of different substances. The carbohydrate substances may be labelled, e.g. with a fluorescent labelling reagent, to impart a charge to the substance, thereby to enable electrophoretic separation, and to enable visualisation of the substances after running of the gel. Visualisation may be effected with the naked eye, but enhanced sensitivity is obtained by viewing with a charge coupled device (CCD).

The present invention concerns a development of such techniques in the form of a further processing step applicable to electrophoretically separated carbohydrate units.

SUMMARY OF THE INVENTION

According to one aspect of the present invention there is provided a method of treating carbohydrate substances, comprising transferring onto a porous membrane by a blotting technique carbohydrate substances labelled with a charged fluorescent labelling reagent which have been run on an electrophoretic gel.

The method enables recovery of charged carbohydrate substances from a gel in a form that is well suited to further treatment or storage, providing a permanent record of electrophoretic separation in the gel. For example, blotted carbohydrate substances can be analysed by probing the blot on the membrane with labelled probes, for instance lectins, sugar specific monoclonal antibodies, viral receptors or other protein probes. Suitable probing techniques are known to those skilled in the art.

The transfer step can be effected using blotting techniques such as are known for blotting proteins from electrophoretic gels, e.g. as discussed in the paper by Jackson and Thompson in Electrophoresis, 1984, 5, 35-42. It is preferred to use an electrotransfer or electroblotting technique, e.g. using semi-dry blot transfer apparatus, which involves contacting the gel with a suitable membrane and applying an electric field to cause resolved materials in the gel to be transferred to the membrane.

A wide range of porous membranes suitable for use in such techniques are commercially available, and are made of materials including activated paper, nitrocellulose, nylon, and polyvinyl difluorone (PVDF), and charged derivatives of such materials. A suitable membrane for use in a particular system can be selected by experiment.

In a further aspect of the invention provides a method of treating carbohydrate substances, comprising applying carbohydrate substances labelled with a charged fluorescent labelling reagent to an electrophoretic gel; running the gel to cause differential migration of different substances; and transferring the substances from the gel onto a porous membrane by a blotting technique.

The gel preferably comprises a relatively dense polyacrylamide gel, having a concentration in the range 15% to 60%, preferably 20% to 40%, although in some cases it may be possible or preferable to use gels of lower concentration.

The gel may be either of uniform concentration or in the form of a gradient gel.

The gel is preferably cross linked, e.g. with N,N' methylenebisacrylamide (bis).

The presently preferred gel comprises a linear polyacrylamide gradient gel having a polyacrylamide concentration (w/v) varying in a continuous gradient from 20% (top) to 40% (bottom). The gel is crosslinked with bis, at a concentration (w/v) varying from 0.53% at the lowest concentration of polyacrylamide to 1.06% at the highest concentration of polyacrylamide. Alternatively, the electrophoretic system described in Neville, Jr., D. M., J. Biol. Chem. 1971, 246, 6328-6334 has been found to give good results.

For good sensitivity the gel is preferably run using a stacking buffer system (also known as moving boundary electrophoresis, multiphasic zone electrophoresis and other names), using techniques known for working with protein and DNA fragments, e.g. as described in the book "Gel electrophoresis of proteins: a practical approach" edited by B D Hames and D Rickwood, published by IRL Press.

The carbohydrate substances are labelled with a charged fluorescent labelling reagent prior to electrophoretic separation, thereby to impart a charge to the substance so as to enable electrophoretic separation, and also to facilitate visualisation of the substances after running of the gel and after transfer to the membrane.

The currently preferred fluorescent labels are aminonaphthalenesulphonic acids with one, two or three substituent suphonic acid groups, particularly 8-aminonaphthalene-1,3,6-trisulphionic acid (known as ANTS for brevity). As described in the copending PCT application No. PCT/GB90/01448 (the disclosure of which application is incorporated herein by reference), use of such labelling materials can enable very good electrophoretic resolution of different carbohydrate substances with very good sensitivity.

The labelling reagent may be attached to sites on the carbohydrate substances, after release if necessary from an attached biomolecule. Alternatively, the biomolecule may be modified in known way to enable incorporation of the labelling reagent.

A carbohydrate substance may be labelled with a labelling reagent such as ANTS by incubating the substance with ANTS and a reducing agent, e.g. sodium cyanoborohydride. For good labelling it is found useful to add the ANTS in solution in a mixture of acetic acid and water, e.g. containing 15 parts by volume of acetic acid to 85 parts by volume of water. ANTS is commercially available, e.g. from Molecular Probes, Eugene, Oreg., which supplies the material in the form of the disodium salt.

After running the gel the labelled carbohydrate substances when illuminated with ultra violet light of suitable wavelength, may be visible with the naked eye in some cases, although better resolution and sensitivity may be obtained by imaging with CCD. Use of a CCD also has the advantage of giving readily quantitated results very quickly. Further, a CCD can be used to view the gel while it is being run.

It is preferred to use a cooled 2-D CCD, operating in slow scan readout. One example of a suitable CCD system is the CCD 2200 Imaging System produced by Astromed Limited, Cambridge, United Kingdom. The CCD is preferably cooled to at least as low as −25° C., with sensitivity being significantly increased by further cooling down as far as −160° C. Typical operation temperatures are in the range −40° C. to −120° C.

The invention is applicable to use on a wide range of carbohydrate structures, including those derived from glycoproteins, proteogylcans, glycolipids, glycosphingolipids, polysaccharides, glycosaminoglycans and other biomolecules, including complex biomolecules containing any of these as a component.

When using ANTS as the labelling reagent, good results have been obtained using an Immobilon-N membrane obtained from Millipore, which is a positively charged derivative of polyvinyl diflurone (PVDF). This material interacts well with the negatively charged ANTS, and results in substantially 100% retention of ANTS labelled carbohydrate substances on the membrane.

The invention will be further described, by way of illustration, in the following Example and by reference to the accompanying drawings, in which.

DESCRIPTION OF PREFERRED EMBODIMENTS

In the following Example 1, reducing sugars which have been labelled with ANTS are separated by polyacrylamide gel electrophoresis and then transferred (blotted) by electrophoresis perpendicular to the gel onto a thin porous membrane to which they adhere. The procedure involves the following steps.

Reaction of ANTS with Reducing Sugars

Figure 1:
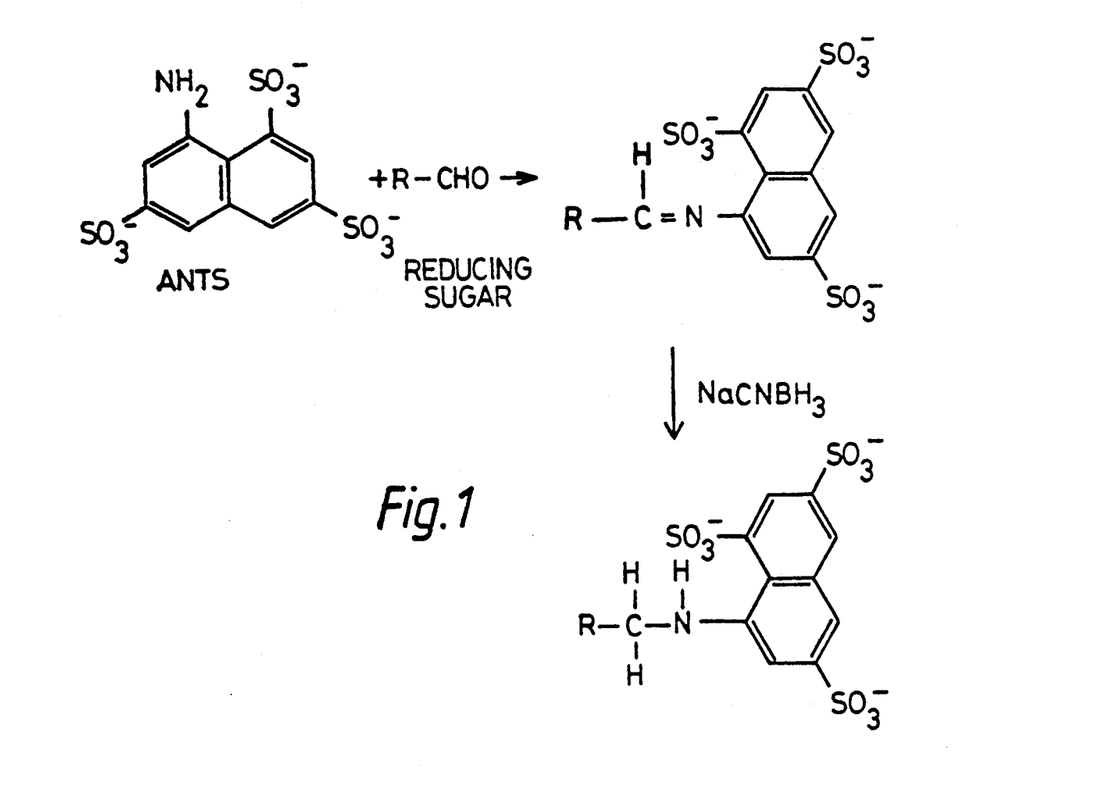
FIG. 1 is an equation illustrating the reaction of ANTS (shown in ionized condition) with a reducing sugar.

FIG. 1 illustrates the reaction of ANTS with a reducing sugar.

The reaction may be achieved by the following procedure.

1. Freeze-dry the reducing sugar(s) in microcentrifuge tube.
2. Add 5 ul 0.2M ANTS (in the form of the disodium salt, obtained from Molecular Probes, Eugene, Ore.) in solution in acetic acid/water. (15:85, v/v).
3. Add 5 ul 1.0M sodium cyanoborohydride in solution in dimethyl sulphoxide.
4. Mix well and incubate at 37° C. for 15 hours (overnight).
5. Freeze-dry the sample by vacuum.
6. Dissolve the sample in a suitable volume of sample buffer i.e. 6M-urea, 0.062M-tris-HCl, pH 6.8.
7. Either store the sample frozen at −70° C. or analyse by electrophoresis immediately.

Electrophoresis of the ANTS Labelled Reducing Sugars

Principle

The ANTS labelled sugars are subjected to electrophoresis in a polyacrylamide gel. The separation is dependent on the molecular weight and the structure of each sugar. A moving boundary (stacking) buffer system is used to give sharp bands and high resolution. This system is based on the method of Laemmli (Nature, 1970, 227, 680–685) but the detergent SDS (sodium dodecyl sulphate) is omitted throughout.

Procedure

1. Set up a vertical slab electrophoretic gel apparatus according to the manufacturers instructions. Use a gel thickness of 0.5 mm.
2. Make a resolving gel consisting of a linear polyacrylamide gradient from 20% w/v (top) to 40% w/v. Make the low concentration acrylamide slution 20% w/v and 0.53% w/v N,N' methylenebis acrylamide (bis) and the high concentration solution 40% w/v and 1.06% w/v bis. Both solutions contain 0.38M Tris-HCl buffer pH 8.55, 0.0167% w/v ammonium persulphate and 0.085% v/v N,N,N',N'-tetramethylenediamine (TEMED). The gel length is 12 cm.
3. Overlayer the gel solution with water and allow the resolving gel to polymerise.
4. Make a stacking gel 2 cm high on top of the resolving gel. The stacking gel solution consists of 3.0% w/v acrylamide, 0.08% w/v bis, 0.12M Tris-HCl buffer pH 6.8, 0.1% w/v ammonium persulphate, 0.1% v/v TEMED. Use a comb to form sample wells in the stacking gel.
5. When the stacking gel is polymerised remove the comb and rinse the sample wells with reservoir buffer (192 mM glycine, 25 mM Tris base, pH 8.3).
6. Load the samples into the wells.
7. Set up the electrophoretic apparatus according to the manufacturer's instructions.
8. Connect the equipment to a DC power supply and electrophorese.
9. Turn off the current.
10. Remove the gel from the mould and photograph using ultra violet illumination, e.g. using a light box. The preferred wavelength of illuminating light is about 370 nm, but good results have been obtained with a broad spectral spread having a maximum wavelength of 302 nm.

This method enables glucose and all of its alphal-4 linked oligomers from maltose to maltoheptaose to be well separated. In addition it also enables the separation of some monosacharides of the same molecular weight but of different structures e.g. Glc from Gal and 6-deoxyGlc from 2-deoxyGlc. It will separate maltose from cellobiose and maltotriose from cellotriose but using the present method it has not been possible to separate Glcalphal-3Glc from Glcbetal-3Glc nor Glcalphal-6Glc from Glcbetal-6Glc.

Up to 27 bands have been observed in an enzymic starch digest (alpha-amylase) on a single gel each differing by a single hexose unit from the next.

Blotting of ANTS Labelled Reducing Sugars

Electrotransfer of ANTS labelled sugars from the gel electrophoretogram to a porous membrane of Immobilon-N is carried out using semi-dry blot transfer apparatus in the following manner.

1. Place a sheet of Whatmann 3MM filter paper wetted with blotting buffer (25 mM Tris base 192 mM glycine) on the lower electrode of the semi-dry blotting apparatus.
2. Place one or more sheets of blotting membrane for instant Immobilon-N or Immobilon-P (Millipore) on top of the filter paper.
3. Place the gel on top of the membrane.
4. Place 5 sheets of wetted filter paper on top of the gel and press with a printers roller to remove air bubbles.
5. Place the upper electrode of the semi-dry blotting apparatus on top of the sandwich.
6. Connect to a DC power pack and electrophorese for 10 minutes at 5 V.

There should be no air bubbles between the various layers of the blotting sandwich.

EXAMPLE 1

Various sugars were labelled with ANTS, as described above, and run on a polyacrylamide electrophoretic gel, as described above. The resulting gel was photographed under UV illumination on a light box having a broad spectral spread of light with a maximum wavelength of 302 nm and the result is shown in FIG. 2.

Figure 2:
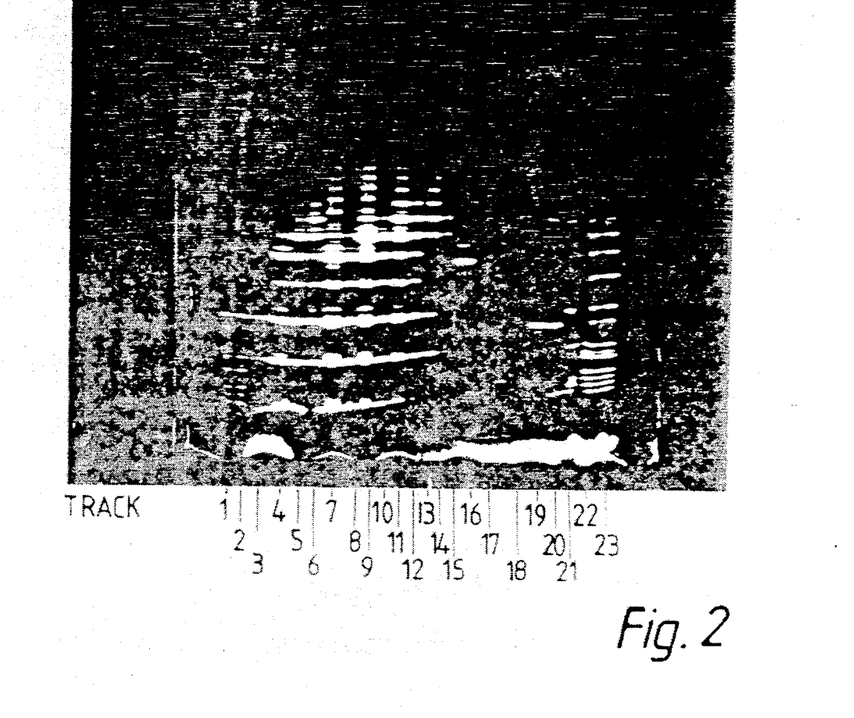
FIG. 2 is a photograph of an electrophoretic gel showing various sugars labelled with ANTS.
Figure 3:
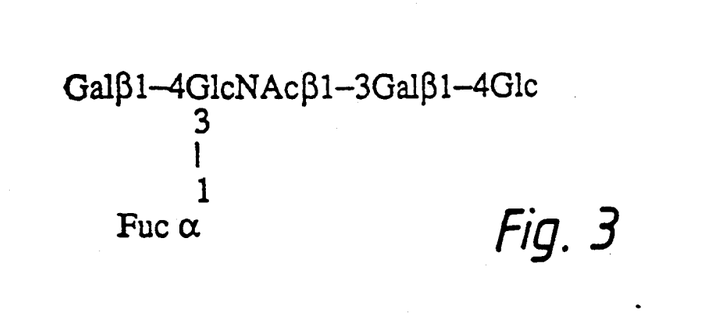
FIGS. 3 and 4 illustrate the structures of two complex, branched sugars used in Example 1.
Figure 4:
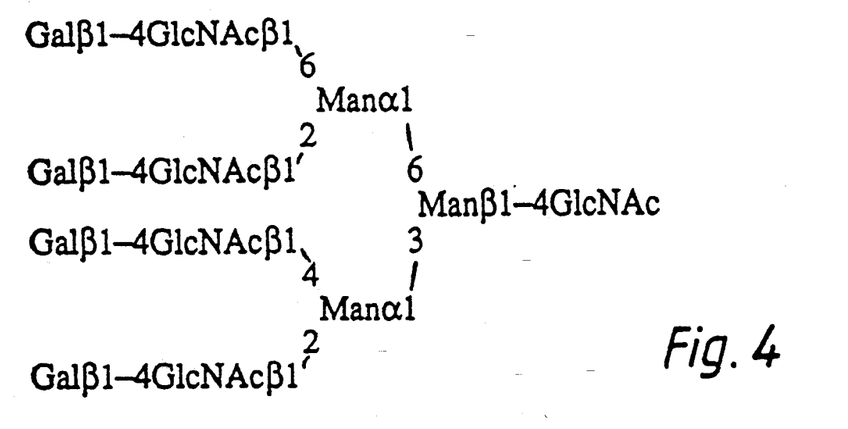

In FIG. 2 the tracks are as follows:
1. Standard mixture (see below)
2. Standard mixture as for track 1
3. 6-deoxy-D-Glc, D-Glc, D-Gal, 6-deoxy-L-Gal (L-fucose) maltose, maltoriose, maltoheptaose
4–14. Starch digested with alpha-amylase (from *Bacillus subtilis*, obtained from Boehringer).
15. Complex sugar 1 (the structure of which is shown in FIG. 3) incubated with beta-calactosidase.
16. Beta-galactosidase.
17. Complex sugar 2 (the structure of which is shown in FIG. 4) incubated with beta-galactosidase.
18. Beta-galactosidase
19. Galbetal-4Gal, Galbetal-6Gal, cellotriose
20. Galbetal-4Gal, Galbetal-6Gal, cellotriose 6deoxyGlc, maltoheptaose blotting.
21. As track 3
22. Standard mixture as for track 1.
23. Standard mixture as for track 1.

The standard mixture consists of equal molar quantities of: maltoheptaose, maltohexaose, maltopentaose, maltotetraose, maltotriose, cellotriose, Galbetal-6Gal, maltose, Galbetal-4Glc (lactose), Galalphal-4Gal, GalNac, Gal, Glc,6-deoxyGlc.

Figure 5:
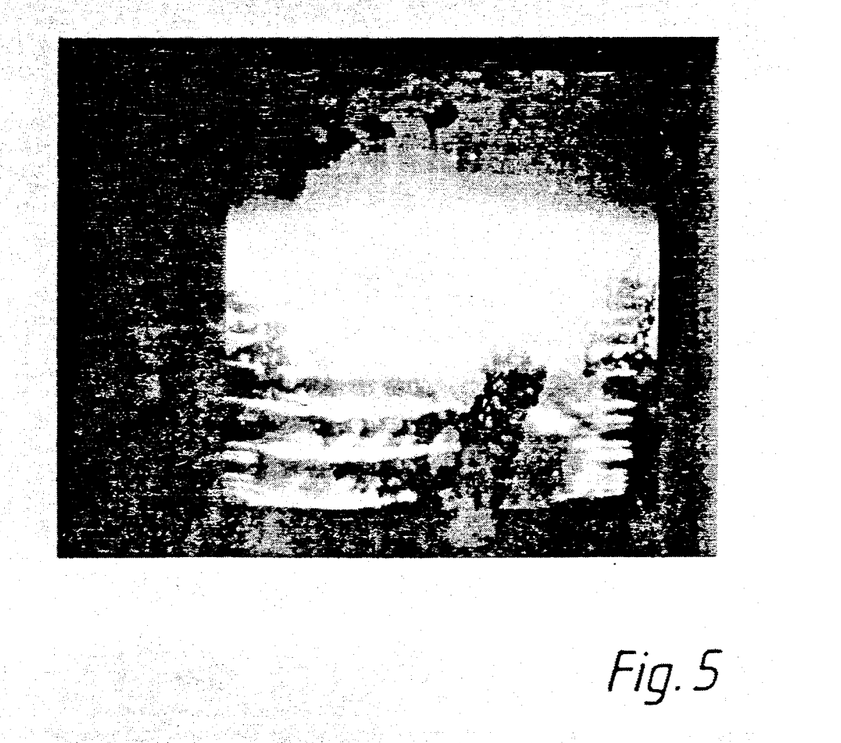
FIG. 5 is a photograph of a sheet of Immobilon-N after electrotransfer of ANTS-labelled sugars from the gel of FIG. 2.

The gel of FIG. 2 was blotted onto a sheet of Immobilon-N. The membrane after blotting was photographed under UV illumination as before and the result is shown in FIG. 5.

Figure 6:
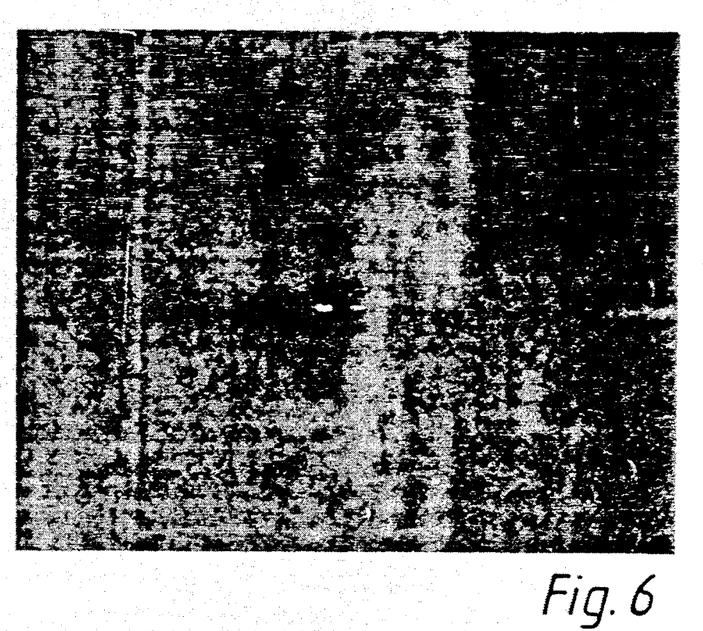
FIG. 6 is a photograph similar to FIG. 2, of the gel after blotting.

FIG. 6 is a photograph similar to FIG. 2, of the gel after the blotting procedure, showing a small quantity of remaining fluorescent ANTS label.

Figure 7:
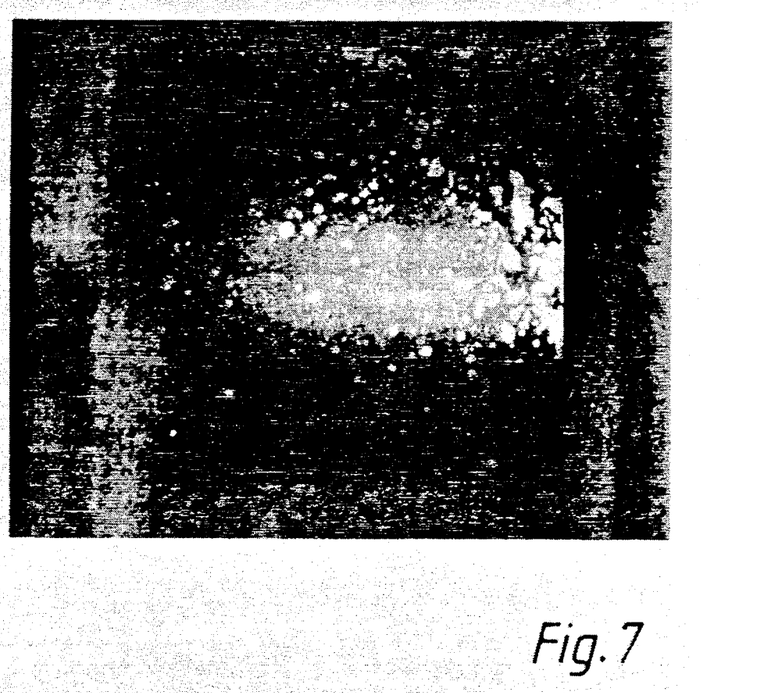
FIG. 7 is a photograph similar to FIG. 5 of a second sheet of Immobilon-N.

FIG. 7 is a photograph similar to FIG. 5 of a second sheet of Immobilon-N membrane placed below (away from the gel) the sheet shown in FIG. 5. This second sheet shows no fluorescence owing to the ANTS, indicating that all the labelled sugar molecules have been trapped by the first sheet of immobilon-N.

All of the sugars mentioned in the specification are D isomers unless otherwise specified.

I claim:

1. A method of quantitatively analyzing unchanged carbohydrate substance mixtures, comprising transferring onto a porous membrane by a blotting technique carbohydrate substances labelled with a changed fluorescent labelling reagent which have been run on an electrophoretic gel.

2. A method according to claim 1, wherein said carbohydrate substances may be glycoproteins, proteoglycans, glycolipids, glycosphingolipids, polysaccharides and glycosaminoglycans.

3. A method according to claim 1, wherein the gel is crosslinked with N,N' methylenebisacrylamide.

4. A method according to claim 1, wherein said electrophoresis is carried out using a stacking buffer system.

5. A method of quantitatively analyzing uncharged carbohydrate substance mixtures, comprising applying carbohydrate substances labelled with a charged fluorescent labelling reagent to an electrophoretic gel; running the gel to cause differential migration of different substances; and transferring the substance from the gel onto a porous membrane by a blotting technique.

6. A method according to claim 5, wherein the electrophoretic gel comprises a polyacrylamide gel having a concentration in the range 15% to 60%.

7. A method according to claim 6, wherein the gel has a concentration in the range of 20% to 40%.

8. A method according to claim 5, wherein said blotting step is effected using an electrotransfer technique.

9. A method according to claim 8, wherein said blotting step is effected using a semi-dry blot transfer apparatus.

10. A method according to claim 5, wherein the porous membrane is selected from the group consisting of activated paper, nitrocellulose, nylon, polyvinyl diflurone, and charged derivatives thereof.

11. A method according to claim 5, said method further comprising the step contacting said porous membrane with a labeled probe.

12. A method according to claim 11, wherein said probe is a protein probe.

13. A method according to claim 5, wherein said carbohydrate substances are labelled with an aminonaphthalenesulphonic acid.

14. A method according to claim 13, wherein said carbohydrate substances are labelled with 8-aminonaphthalene-1,3,6-trisulphonic acid.

15. A method according to claim 14, wherein the porous membrane comprises a positively charged derivative of polyvinyl diflurone.

* * * * *